(12) United States Patent
Wu

(10) Patent No.: US 7,137,287 B2
(45) Date of Patent: Nov. 21, 2006

(54) STAGED ELECTRODE CARRIER OF AN $O_2$ SENSOR

(75) Inventor: Hsiao Chung Wu, Taoyuan (TW)

(73) Assignee: Sentec E&E Co., Ltd., Taoyuan (TW)

( * ) Notice: Subject to any disclaimer, the term of this patent is extended or adjusted under 35 U.S.C. 154(b) by 19 days.

(21) Appl. No.: 10/889,634

(22) Filed: Jul. 13, 2004

(65) Prior Publication Data

US 2006/0010960 A1 Jan. 19, 2006

(51) Int. Cl.
*G01N 7/00* (2006.01)
(52) U.S. Cl. ..................... 73/31.05; 73/23.31
(58) Field of Classification Search ............. 73/19.01, 73/19.1, 19.11, 31.05, 23.31
See application file for complete search history.

(56) References Cited

U.S. PATENT DOCUMENTS 5,707,504 A * 1/1998 Jyouno et al. ............. 204/428
2002/0070736 A1 * 6/2002 Nakae et al. ............... 324/717

* cited by examiner

*Primary Examiner*—Daniel S. Larkin

(57) ABSTRACT

A staged electrode carrier of an $O_2$ sensor comprises a sensor; a detecting end carrier installed in the sensor; the detecting end carrier having a positive lead, a negative lead and a channel communicated to atmosphere; one end of the positive lead of the detecting end carrier having a positive interface exposing in the channel so as to contact the atmosphere and one end of the detecting end carrier having a negative interface exposing from an outer wall of the detecting end carrier to contact gas to be measured; and a transferring end carrier installed in the sensor having a positive lead and a negative lead. A detecting end carrier is made of zirconium oxide, and a transferring end carrier is made of $Al_2O_3$, CaO or MgO.

16 Claims, 8 Drawing Sheets

STAGED ELECTRODE CARRIER OF AN $O_2$ SENSOR

FIELD OF THE INVENTION

The present invention relates to an $O_2$ sensor, and particular to a staged electrode carrier of an $O_2$ Sensor, wherein a detecting end carrier is made of zirconium oxide $ZrO_2$ and a transferring end carrier is made of $Al_2O_3$, CaO or MgO. The two carriers are made of positive leads and negative leads for detecting oxygen density of the gas to be measured.

BACKGROUND OF THE INVENTION

An $O_2$ sensor is in general installed in the oil and air inlet ends or the exhausting tubes of the engines of cars and motorcycles for detecting the air to fuel ratios of the oil and air inlet ends or the oxygen contained in the waste gas exhausting ends. In other words, oxygen density in the gas (oil or wasted gas) to be measured is detected by the $O_2$ sensor so as to supply control signals to the engine control unit to adjust the air to fuel ratio to an optimum value. Thereby, the exhaustion of harmful material in the air can be reduced.

It is appreciated that the conventional $O_2$ sensor can be classified into a heating sensor and a non-heating sensor. The difference between the two is whether a thermal coupler is added in the sensor. The heating $O_2$ sensor causes the electrode carriers in solid electrolyte materials to be heated rapidly to a temperature over 350° C. so that the $O_2$ sensor can detect the air to fuel ratio or the potential signals of the sensor. On the contrary, the non-heating $O_2$ sensor heats the electrode carriers by heat from the oil gas or wasted gas. Thereby, the reaction for sensing the potential signal is slow, but it can achieve a normal detection ability when the engine is actuated for a time period.

Moreover, the heating or non-heating $O_2$ sensor must be added with a solid electrolytic electrode isolating carrier. Conventionally, the electrode isolating carrier is made of zirconium oxide ($ZrO_2$). The conventional sensor is a solid electrolytic high temperature $O_2$ sensor which is made of a single long strip-like electrode carrier. A channel communicated to an external atmosphere is formed within the carrier and the carrier is formed with a positive lead and a negative lead. The positive interface is in contact with the atmosphere through the channel and the negative interface is in contact with the waste gas. The positive interface and negative interface are chemically reacted with the solid electrolytic zirconium oxide carrier so as to decompose the oxygen in the atmosphere and gas to be measured to generate a voltage. The voltage is transferred through a single zirconium oxide carrier so as to detect the oxygen density of the gas to be measured or the air to fuel ratio.

However, it is known that in the whole carrier, only the peripheries of the positive interface and negative interface are necessary to generate the voltage by using the zirconium oxide. Other voltage transferring portions of the carrier are unnecessary to use zirconium oxide as a solid electrolyte. Furthermore, since the price of zirconium oxide is very expensive; and the electrode carrier in the conventional $O_2$ sensor uses zirconium oxide as a solid electrolyte, the price of the sensor is high and the cost can not be reduced.

SUMMARY OF THE INVENTION

To overcome the prior art defect, the present invention provides a staged electrode carrier of an $O_2$ sensor, wherein the amount of zirconium oxide is reduced so as to reduce the cost of the $O_2$ sensor.

Another object of the present invention is to provide a staged electrode carrier of an $O_2$ sensor, wherein the electrode carrier is made as different stages and includes a detecting end carrier with a smaller volume and being made of zirconium oxide and a transferring end carrier having a larger volume and being made of $Al_2O_3$, CaO or MgO.

By the above method, the amount of zirconium oxide is greatly reduced and the cost of the electrode carrier is also reduced. Meanwhile, the peripheries of the positive interface and negative interface of the detecting end carrier are retained for generating a voltage by the zirconium oxide. Moreover, it is only necessary to change the material of the voltage transferring portion of the electrode carrier into $Al_2O_3$, CaO or MgO as a transferring end carrier, which is sufficient to protect the positive lead and negative lead. Thereby, the positive interface and negative interface can transfer voltage steadily to external signal receiving end.

Besides, the positive leads and negative leads are installed both on the detecting end carrier and transferring end carrier. The two carriers in the body of the $O_2$ sensor have connecting surfaces for the positive leads and negative lead so as to form a structure for transferring signals.

Moreover, in the present invention, a channel communicating with the external atmosphere is formed in the detecting end carrier so that the positive interface of the positive lead projects into the channel to contact the external atmosphere and the negative interface of the negative lead projects from an outer wall of the detecting end carrier to contact the gas to be measured. Thereby, the oxygen densities in the external atmosphere and the gas to be measured can be detected and compared so as to generate voltages of different potential differences.

Moreover, the transferring end carrier of the present invention is formed with a channel communicating with an open type channel. Therefore, the external atmosphere can successfully flow into the channel of the detecting end carrier to be measured in the positive interface.

Furthermore, in the present invention, a heating coupling heater can be added to the transferring end carrier. By the radiation effect and heat convection effect, the body of the sensor can be heated to make the two carriers have temperatures over 350° C., which is in the range of normal working temperature.

The various objects and advantages of the present invention will be more readily understood from the following detailed description when read in conjunction with the appended drawings.

DETAILED DESCRIPTION OF THE INVENTION

In order that those skilled in the art can further understand the present invention, a description will be described in the following details. However, these descriptions and the appended drawings are only used to cause those skilled in the art to understand the objects, features, and characteristics of the present invention, but not to be used to confine the scope and spirit of the present invention defined in the appended claims.

Figure 1:
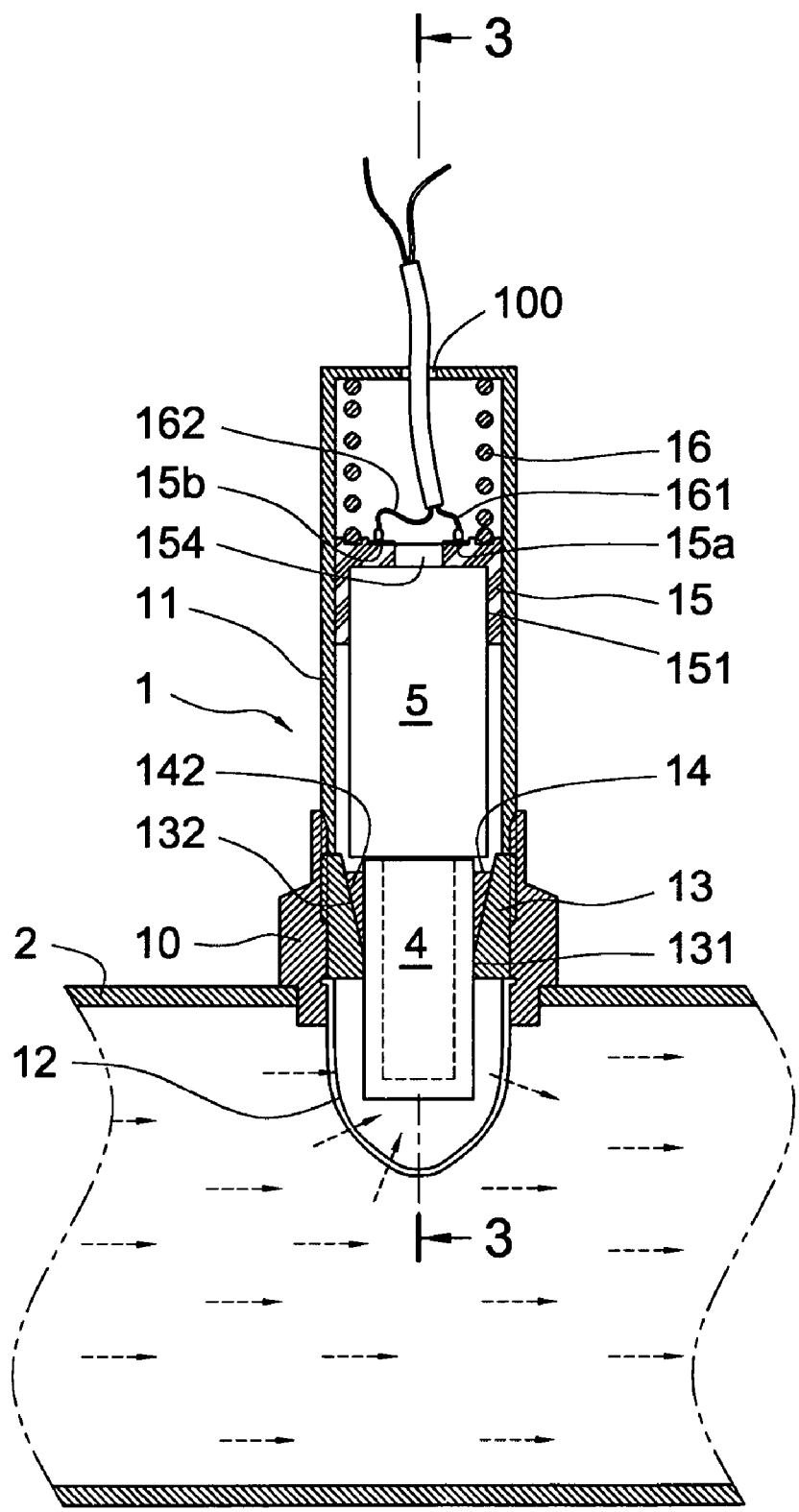
FIG. 1 is a cross sectional view of an embodiment of the $O_2$ sensor of the present invention, wherein the $O_2$ sensor is embedded to the fluid tube wall of a gas to be measured and a body of the $O_2$ sensor is installed with a detecting end carrier and a transferring end carrier.

Referring to FIG. 1, the $O_2$ sensor of the present invention is illustrated. The $O_2$ sensor includes a body 1. The body 1 has a base 10. A top of the base 10 is combined with a cover 11 and a lower side of the base 10 is connected to the ventilating mask 12. The base 10 is embedded within a fluid tube wall 2 of a gas to be measured and causes the ventilating mask 12 to be embedded into the fluid tube wall 2.

The fluid tube wall 2 can be a wall of a gas inlet stub of an engine of a car or a motorcycle, or a wall of a gas exhausting tube of an engine, etc., so that the $O_2$ sensor can detect the mixing ratio of oil and air in the engines or the oxygen-contained in the exhausting end.

In the present invention, the body 1 can be installed with a detecting end carrier 4 and a transferring end carrier 5 (referring to FIG. 1).

Figure 2:
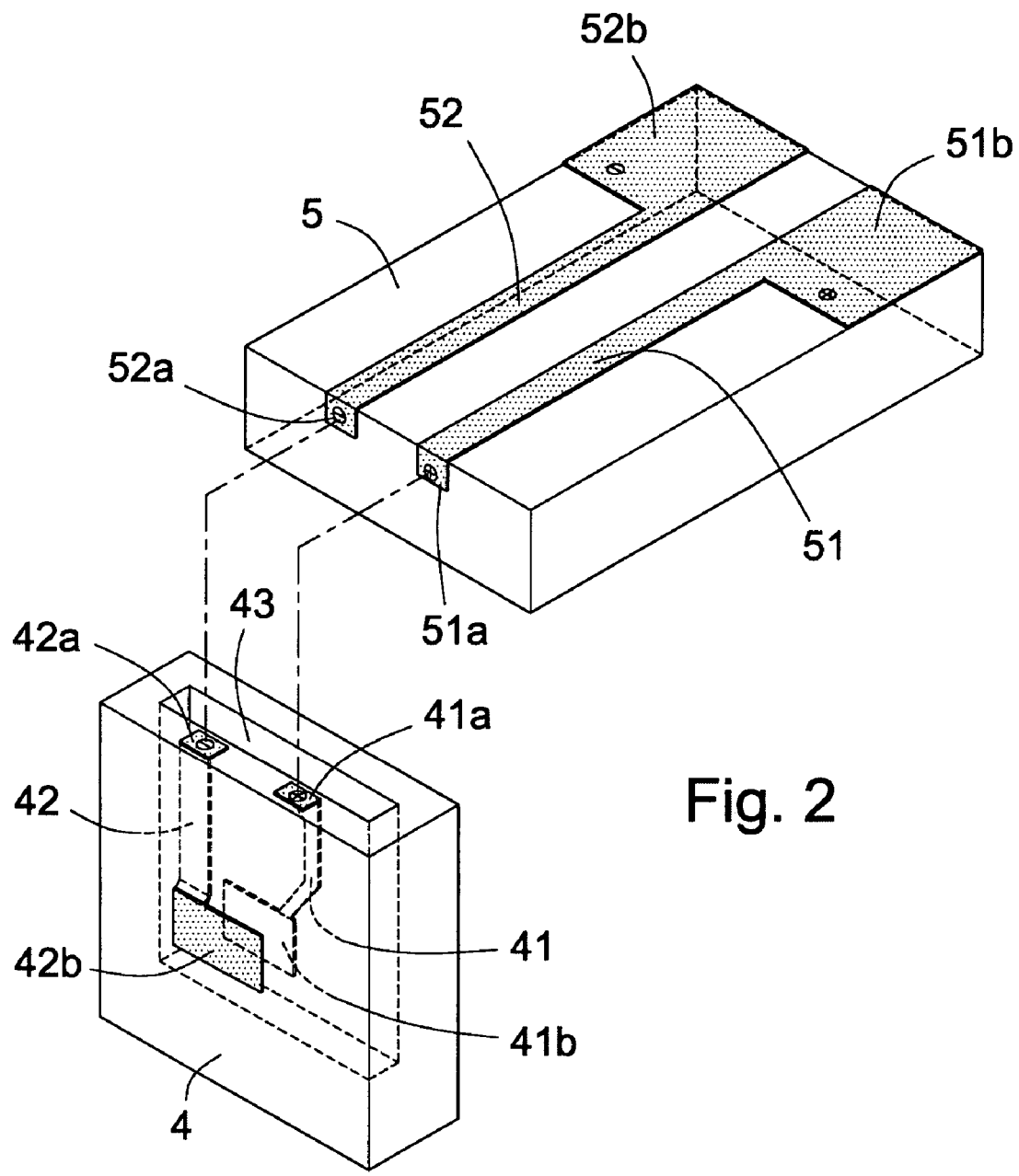
FIG. 2 is an exploded perspective view of the staged carriers, wherein the detecting end carrier is formed with a channel and the detecting end carrier and transferring end carrier are installed with respective positive leads and negative leads.

The detecting end carrier 4 is made of electrolyte type zirconium oxide ($ZrO_2$). The detecting carrier 4 is embedded with a positive lead 41 and a negative lead 42 (see FIG. 2). A channel 43 connected to atmosphere is installed within the detecting end carrier 4.

A positive lead 41 has a positive connecting surface 41a at one end thereof, which projects form a wall of the detecting end carrier 4. The other end of the positive lead 41 is installed with a positive interface which 41b projects into the channel 43.

The negative lead 42 in the detecting end carrier 4 has a negative connecting surface 42a at one end thereof, which projects from a wall of the detecting end carrier 4 and the other end thereof is formed with a negative interface 42b, which projects from an outer wall of the detecting end carrier 4.

Figure 3:
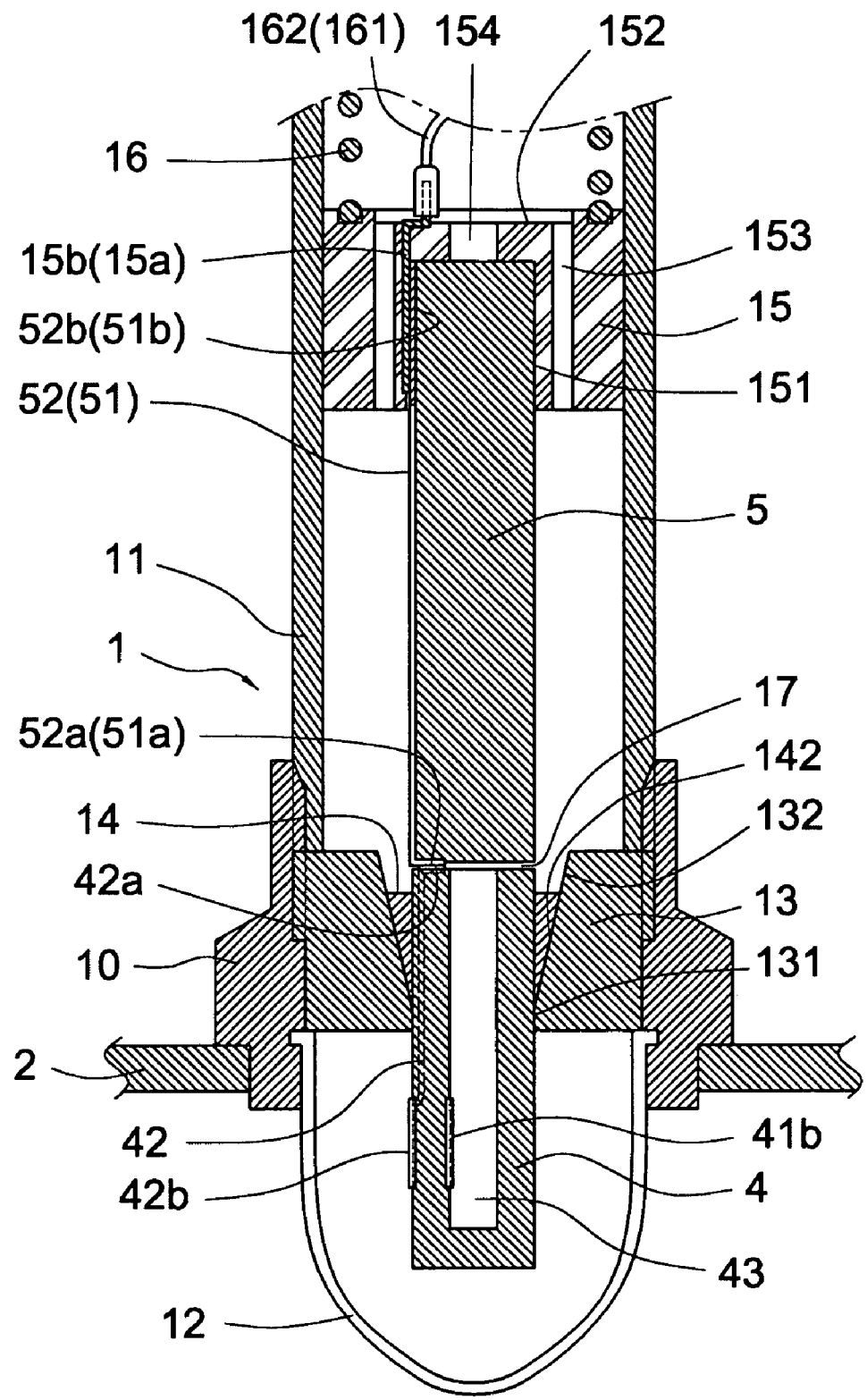
FIG. 3 is a cross sectional view along line 3—3 of FIG. 1, wherein an embedding seat and an insertion ring are installed between a body of the $O_2$ sensor and the detecting end carrier and the transferring end carrier is placed in the body.

The base 10 of the body 1 is locked with an embedding seat 13 therein (referring to FIGS. 1 and 3). The embedding seat 13 has a hole 131. The detecting end carrier 4 passes through the hole 131. One side of the hole 131 extends with a tapered wall 132. An outer wall of the detecting end carrier 4 is firmly secured with an inserting ring 14 having a tapered outer wall 142. The tapered outer wall 142 of the insertion ring 14 resists against the tapered wall 132 of the embedding seat 13 so as to stabilize the detecting end carrier 4 to the base 10 of the body 1. Thereby, the negative interface 42b on the detecting end carrier 4 can contact the gas to be measured in the fluid tube wall 2 through the ventilating mask 12.

The transferring end carrier 5 may be selected from one of $Al_2O_3$, CaO, and MgO. In that, $Al_2O_3$ is the cheapest, next is CaO, and MgO is the most expensive. Any one of the three metal oxides can be selected for making the transferring end carrier 5. The price of the transferring end carrier 5 is cheaper than that of detecting end carrier 4 ($Zr O_2$). The volume of the transferring end carrier 5 is smaller than that of the detecting end carrier 4. Therefore, the cost of the $O_2$ sensor is greatly reduced. Meanwhile, the transferring end carrier 5 is embedded with a positive lead 51 and a negative lead 52 (referring to FIG. 2).

Two ends of the positive lead 51 in the transferring end carrier 5 are formed with positive connecting surfaces 51a and 51b, respectively, which projects from two walls of the transferring end carrier 5.

The two ends of the negative lead 52 in the transferring end carrier 5 are formed with negative connecting surfaces 52a, 52b which also project from two outer walls of the transferring end carrier 5.

The cover 11 of the body 1 is movably installed with a conductive supporting seat 15 (referring to FIGS. 1 and 3). An embedding groove 151 is formed in the conductive supporting seat 15 for receiving one end of the transferring end carrier 5. The conductive supporting seat 15 has a positive signal conductive sheet 15a and a negative signal conductive sheet 15b which pass through the top wall 152 and the embedding groove 151 so that the positive connecting surface 51b of the transferring end carrier 5 is in contact with the positive signal conductive sheet 15a and the negative connecting surface 52b is in contact with the negative signal conductive sheet 15b. The positive signal conductive sheet 15a is connected to a positive signal wire 161 and the negative signal conductive sheet 15b is connected to the negative signal wire 162 so as to be connected to external signal receiving ends.

A top of the conductive supporting seat 15 is installed with a spring 16 to compress an inner wall of the cover 11, as shown in FIG. 1 so that the conductive supporting seat 15 can elastically push the transferring end carrier 5 so that the positive connecting surface 51a and negative connecting surface 52a of the transferring end carrier 5 tightly press upon the positive connecting surface 41a and negative connecting surface 42a of the detecting end carrier 4.

The leads 41, 42, 51, 52 and the connecting surfaces 41a, 42a, 51a, 52a of the detecting end carrier 4 and transferring end carrier 5 can be made as platinum sheets. When the connecting surfaces 51a, 41a, 52a, 42a are connected to one another, a ventilating gap 17 is formed between the transferring end carrier 5 and the detecting end carrier 4 (referring to FIG. 3). Meanwhile, a plurality of vent holes 153, 154 are formed on the conductive supporting seat 15, as shown in FIG. 3. The vent holes 153, 154 are communicable with the external air through the opening 100 in the cover 11 (referring to FIG. 1). Furthermore, air is guided through the ventilating gap 17 to enter into the channel 43 of the detecting end carrier 4 so that the positive interface 41*b* exposed within the channel 43 is in contact with the air.

By the above mentioned arrangement, in detection, the positive interface 41*b* on the detecting end carrier 4 will detect the amount of oxygen in the atmosphere and the negative interface 42*b* on the detecting end carrier 4 detects the amount of oxygen within the gas to be measured in the fluid tube wall 2. Thereby, the oxygen in the atmosphere and gas to be measured are decomposed into oxide ions of different potential differences. By the detecting end carrier 4 being made of zirconium oxide ($ZrO_2$) to induce chemical reaction, the oxygen (amount of oxide ions) contained in the atmosphere and gas to be measured are compared so as to generate voltage signals of different potential differences. By the connections of the positive lead 41 and negative lead 42 in the detecting end carrier 4 and the positive lead 51 and the negative lead 52 of the transferring end carrier 5, and the positive signal conductive sheet 15*a* and negative signal conductive sheet 15*b* of the conductive supporting seat 15, the voltage signals from the positive and negative electrodes are transferred to external signal receiving ends through the positive and negative signal wires 161, 162. The signal receiving end may be, for example, an engine control unit (ECU) for adjusting an optimum air to fuel ratio so as to reduce the exhausting amount of harmful material in the waste gas.

Figure 4:
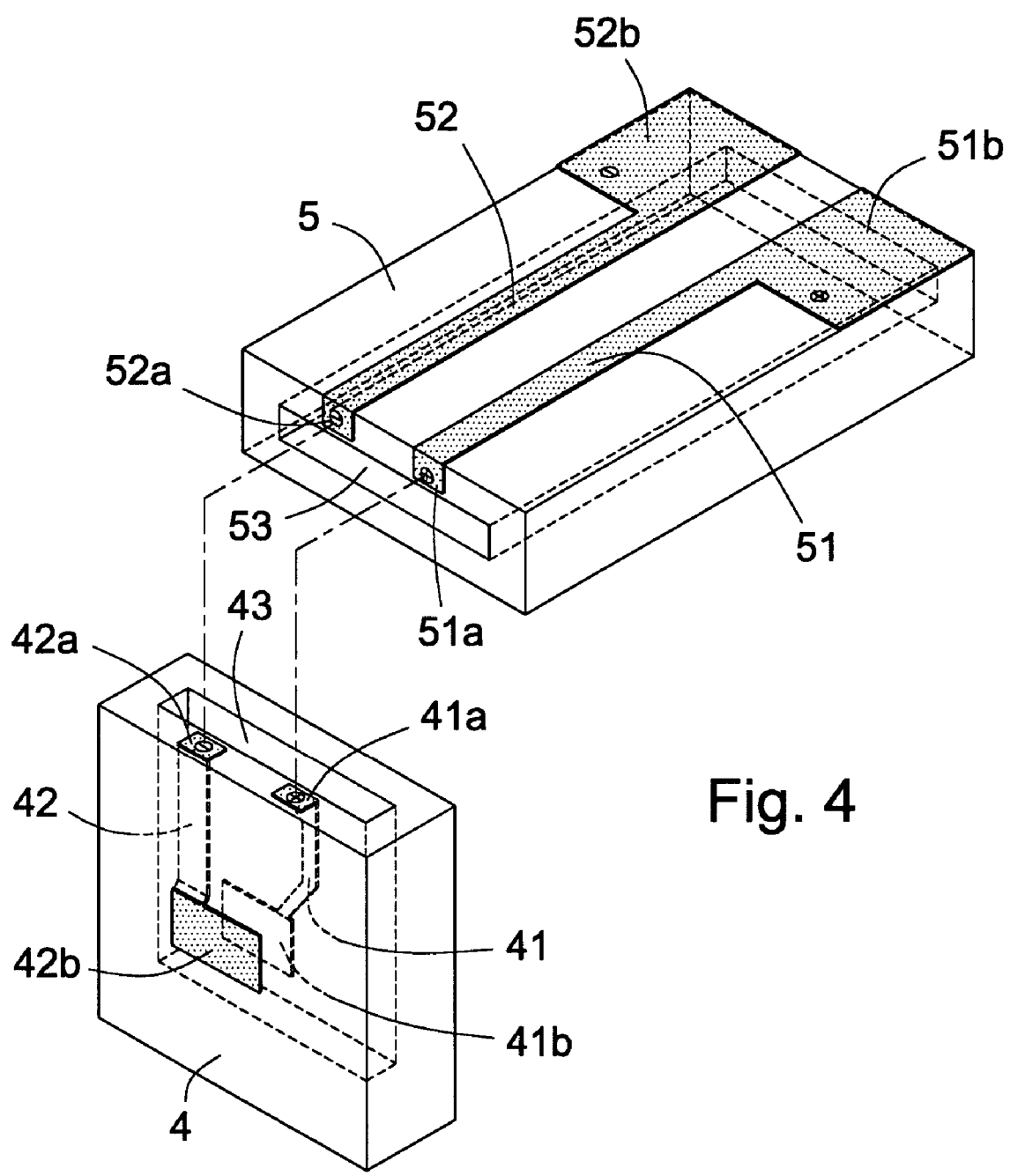
FIG. 4 is an exploded perspective view of another staged carrier, wherein the transferring end carrier is added with a communicable groove.
Figure 5:
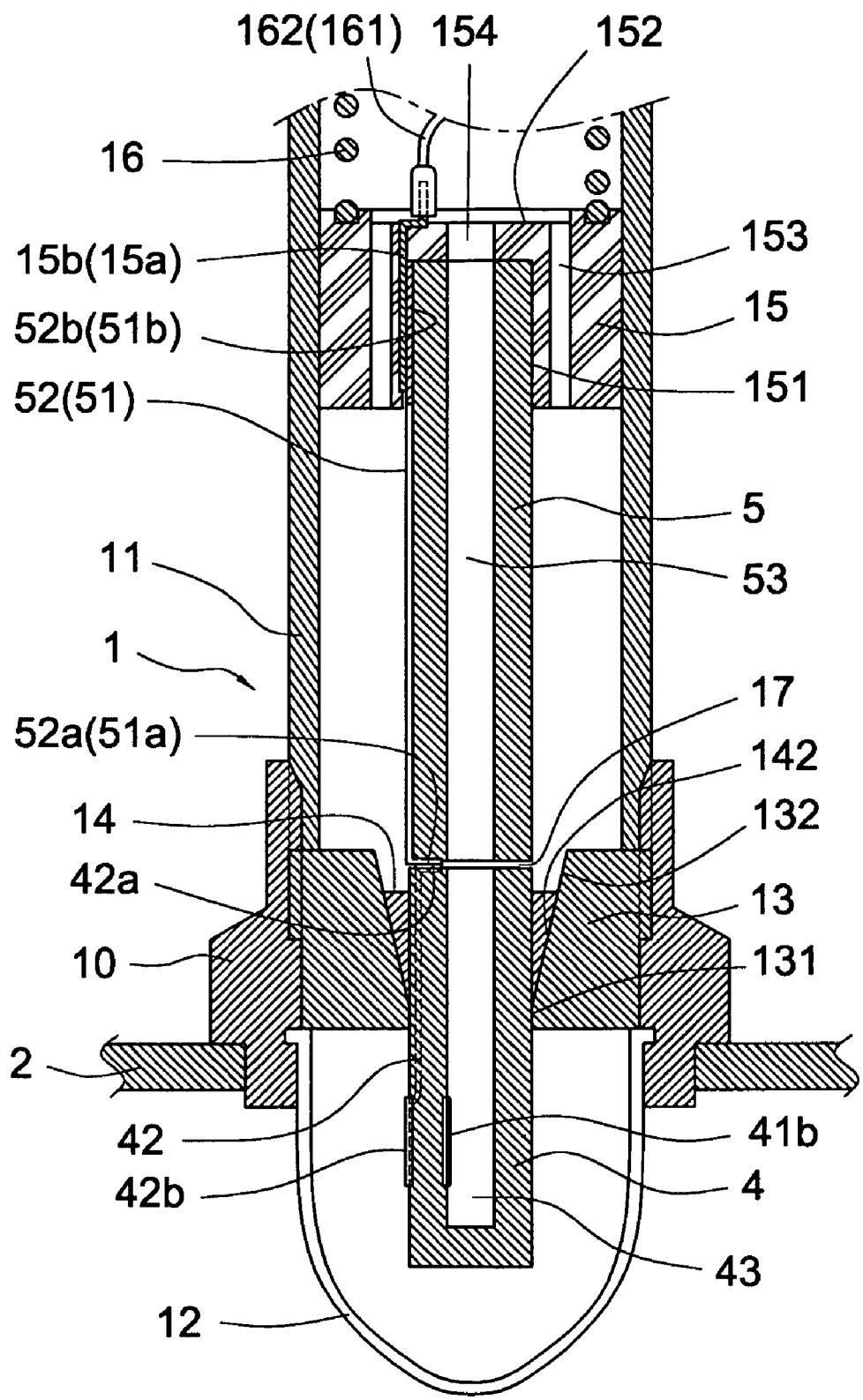
FIG. 5 is a cross sectional view of FIG. 4, wherein the communicable groove of the transferring end carrier is communicable to the channel of the detecting end carrier.

Otherwise, in the present invention, the transferring end carrier 5 can be formed with a communicable groove 53 (referring to FIG. 4) which is communicable within the channel 43 of the detecting end carrier 4 (referring to FIG. 5). Thereby, the transferring end carrier 5 is communicated to atmosphere through the vent 154 of the conductive supporting seat 15 and the opening 100 of the cover 11 (referring to FIG. 1). Thereby, it serves to assist the ventilation gap 17 between the transferring end carrier 5 and the detecting end carrier 4 so that the external air is supplied to the channel 43 sufficiently. Thereby, the positive interface 41*b* has sufficient oxygen for detection within the atmosphere.

Figure 6:
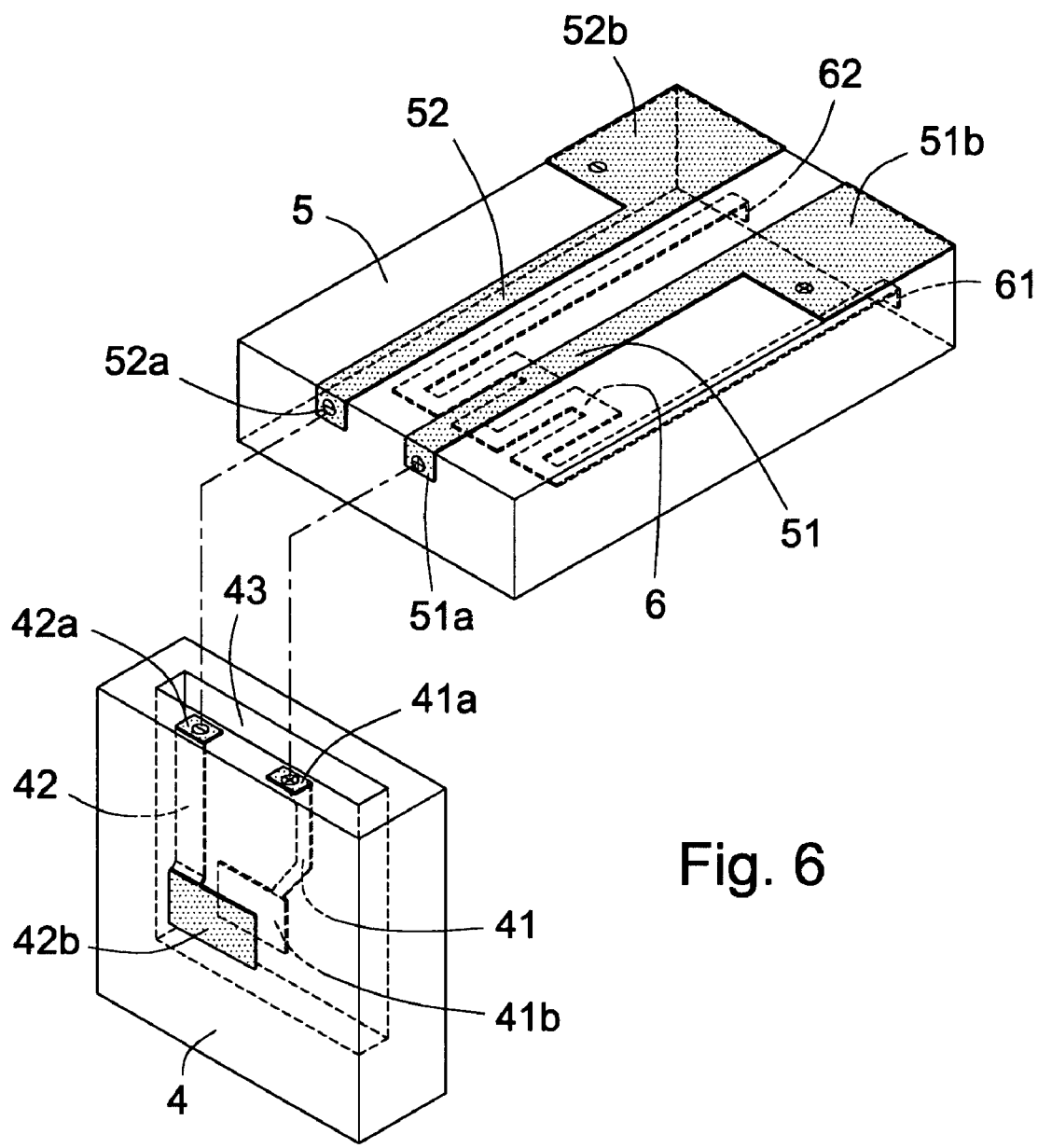
FIG. 6 is an exploded perspective view of another staged carrier, wherein the transferring end carrier is added with a heating coupling heater.
Figure 7:
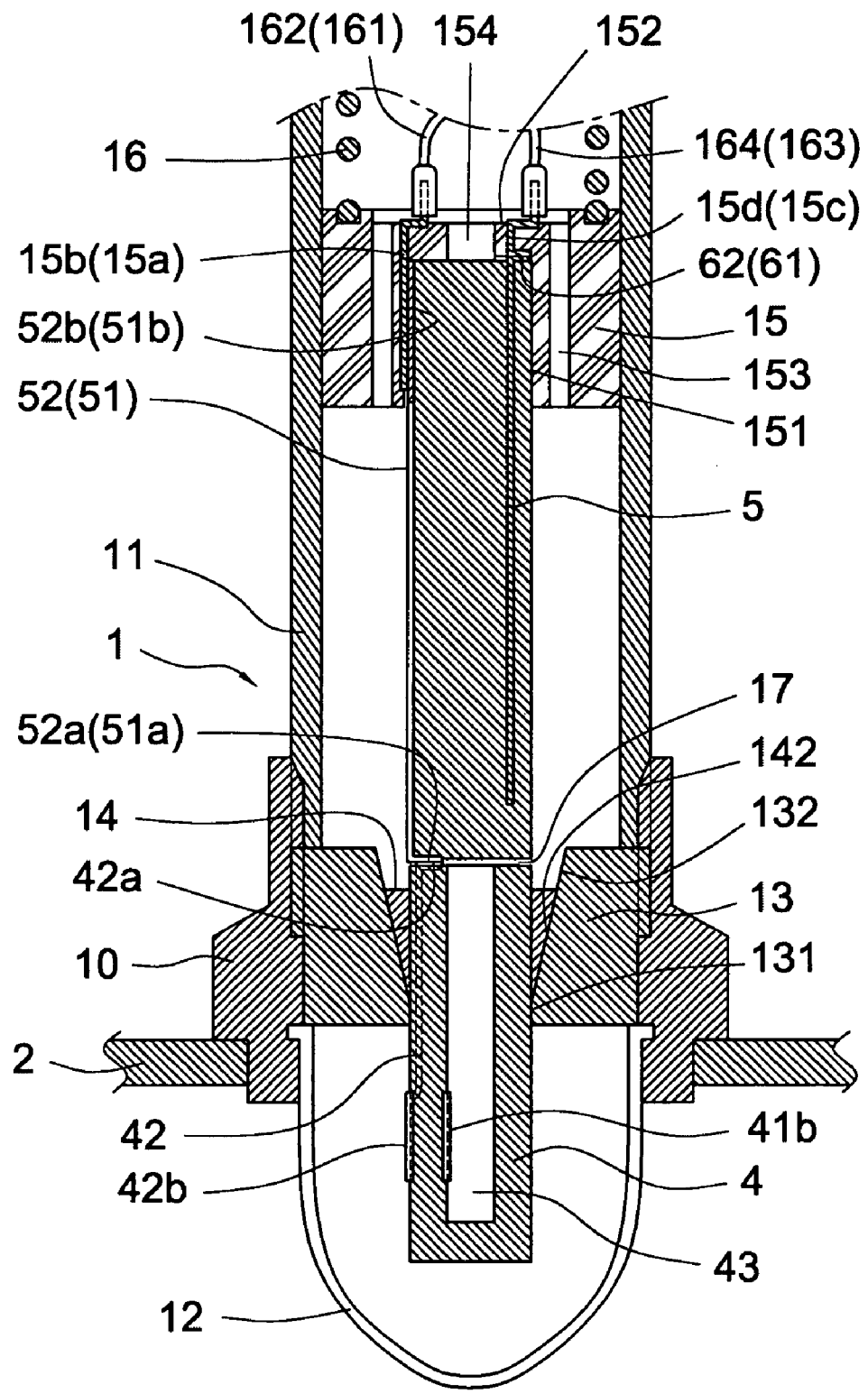
FIG. 7 is a cross sectional view of FIG. 6, wherein the heating coupling heater is embedded within a transferring end carrier without a communicable groove and is connected to a power wire.
Figure 8:
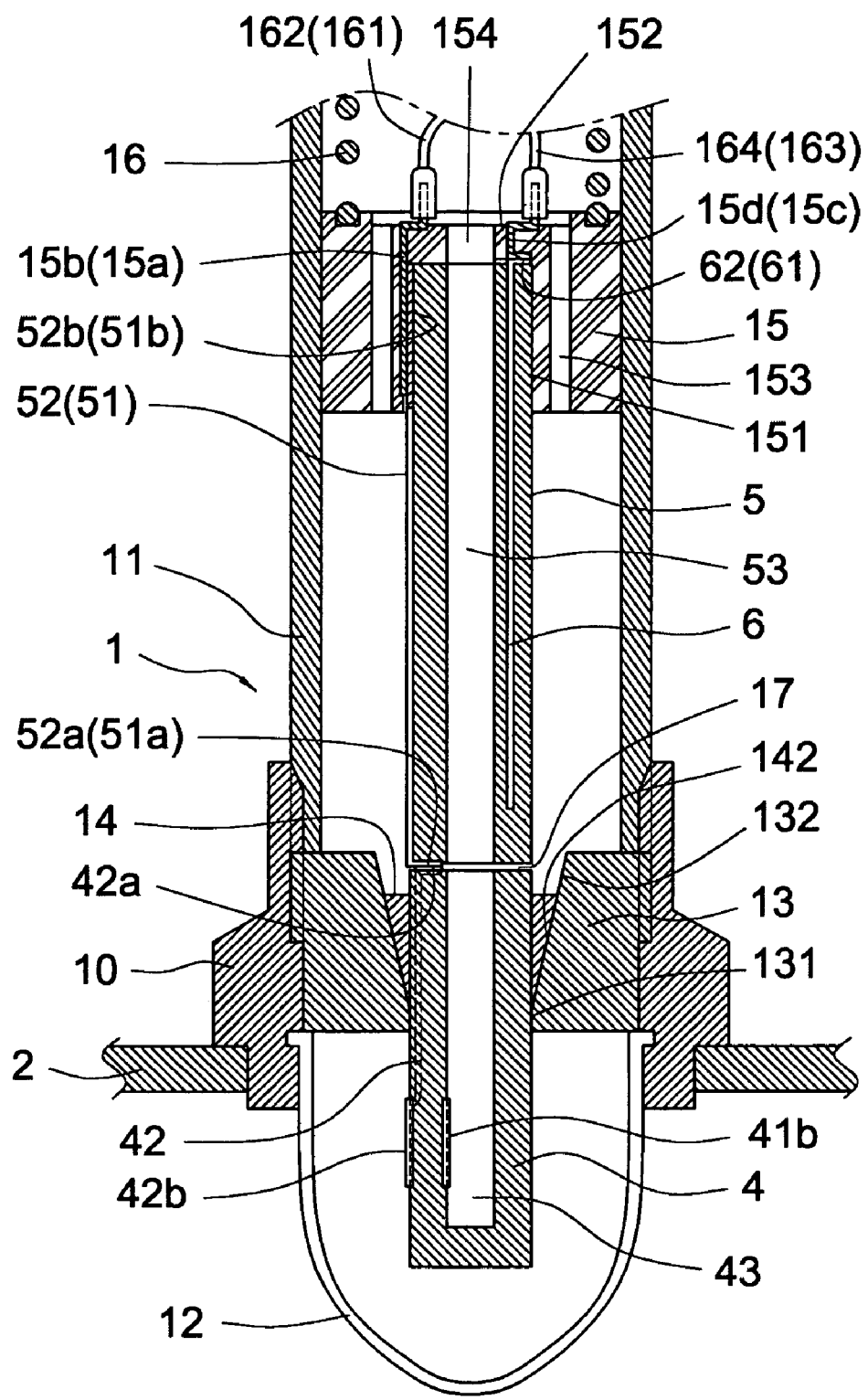
FIG. 8 is a cross sectional view of another embodiment of the present invention, wherein a heating coupling heater is embedded within a transferring end carrier with a communicable groove.

Furthermore, if the communicable groove 53 is not installed in the transferring end carrier 5, the transferring end carrier 5 can be installed with a thermal coupling heater 6, see FIG. 6. The heater 6 can have a positive power joint 61 and a negative power joint 62, which project from a lateral surface of the transferring end carrier 5 (referring to FIG. 7) and are in contact with the positive signal conductive sheet 15*c* and negative signal conductive sheet 15*d* of the conductive supporting seat 15. The connecting ends of the positive signal conductive sheet 15*c* and negative signal conductive sheet 15*d* can be connected to an external power supply through the positive power wire 163 and negative power wire 164. The power supply may be a battery of a car or a motorcycle so as to supply power to actuate the heater 6 to generate heat energy. By the heat conduction and convection in the body 1, the transferring end carrier 5 and detecting end carrier 4 are heated rapidly to a normal working temperature over 350° C. Meanwhile, the way for embedding a thermal coupling heater 6 into the transferring end carrier 5 can be used in the structure of the transferring end carrier 5 having a communicable groove 53, see FIG. 8.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A staged electrode carrier of an $O_2$ sensor comprising:
a sensor having a body;
a detecting end carrier installed in the sensor; the detecting end carrier having a positive lead, a negative lead, and a channel communicated to an external atmosphere; one end of the positive lead of the detecting end carrier having a positive interface projecting into the channel so as to contact the atmosphere and one end of the detecting end carrier having a negative interface projecting from an outer wall of the detecting end carrier to contact gas to be measured; and
a transferring end carrier installed in the sensor having a positive lead and a negative lead.

2. The staged electrode carrier of an $O_2$ sensor as claimed in claim 1, wherein the volume of the detecting end carrier is smaller than that of the transferring end carrier.

3. The staged electrode carrier of an $O_2$ sensor as claimed in claim 1, wherein the detecting end carrier [4] is made of $ZrO_2$ of potential solid electrolyte type.

4. The staged electrode carrier of an $O_2$ sensor as claimed in claim 1, wherein the outer wall of the detecting end carrier is installed with an insertion ring; a tapered wall of the insertion ring is adhered to an inclined wall of an embedding seat in the body of the sensor so as to fix the detecting end carrier.

5. The staged electrode carrier of an $O_2$ sensor as claimed in claim 1, wherein the transferring end carrier is made of $Al_2O_3$.

6. The staged electrode carrier of an $O_2$ sensor as claimed in claim 1, wherein the transferring end carrier is made of CaO.

7. The staged electrode carrier of an $O_2$ sensor as claimed in claim 1, wherein the transferring end carrier is made of MgO.

8. The staged electrode carrier of an $O_2$ sensor as claimed in claim 1, wherein connecting surfaces of the positive lead and the negative lead of the transferring end carrier project from the transferring end carrier.

9. The staged electrode carrier of an $O_2$ sensor as claimed in claim 8, wherein the positive lead and the negative lead of the transferring end carrier are connected to the positive lead and negative lead of the detecting end carrier.

10. The staged electrode carrier of an $O_2$ sensor as claimed in claim 8, wherein the positive lead and negative lead of the transferring end carrier are in contact with two conductive sheets of a conductive supporting seat in the body of the sensor; and one end of each conductive sheet projects from a top of the conductive supporting seat and are connected to a positive signal wire and a negative signal wire so as to be connected to an external receiving ends.

11. The staged electrode carrier of an $O_2$ sensor as claimed in claim 10, wherein a top of the conductive supporting seat is installed with a spring.

12. The staged electrode carrier of an $O_2$ sensor as claimed in claim 1, wherein a ventilating gap is formed at a connection of the transferring end carrier and the detecting end carrier, ventilating gas is communicable to a channel within the detecting end carrier and the atmosphere outside of the body of the sensor.

13. The staged electrode carrier of an $O_2$ sensor as claimed in claim 12, wherein an open communicable groove is installed in the transferring end carrier, which is connected to the channel of the detecting end carrier and the atmosphere outside of the body of the sensor.

14. The staged electrode carrier of an O$_2$ sensor as claimed in claim 1, wherein a heating coupling heater is installed within the transferring end carrier.

15. The staged electrode carrier of an O$_2$ sensor as claimed in claim 14, wherein the heating coupling heater has a positive power joint and a negative power joint which project from a surface of the transferring end carrier.

16. The staged electrode carrier of an O$_2$ sensor as claimed in claim 15, wherein the positive power joint and the negative power joint are connected to a positive signal conductive sheet and a negative power conductive sheet, respectively, in a conductive supporting seat in the body of the sensor; and the positive power conductive sheet and the negative power conductive sheet have a positive power wire and a negative power wire, respectively, to be further connected to an external power supply end.

* * * * *